(12) United States Patent
Ullman

(10) Patent No.: US 6,569,106 B1
(45) Date of Patent: May 27, 2003

(54) MEDICAL GUIDE WIRE CONTAINMENT DEVICE

(76) Inventor: Joseph M. Ullman, 17 White Rock Dr., Falmouth, ME (US) 04105

( * ) Notice: Subject to any disclaimer, the term of this patent is extended or adjusted under 35 U.S.C. 154(b) by 0 days.

(21) Appl. No.: 09/697,369

(22) Filed: Oct. 26, 2000

Related U.S. Application Data

(60) Provisional application No. 60/222,508, filed on Aug. 2, 2000.

(51) Int. Cl.[7] .............................. A61B 5/00; A61B 25/00
(52) U.S. Cl. ....................................... 600/585; 206/634
(58) Field of Search ...................... 206/364; 198/465.1; 600/585; 604/171

(56) References Cited

U.S. PATENT DOCUMENTS

| | | | | |
|---|---|---|---|---|
| 5,125,416 | A | * 6/1992 | Phillips | 600/585 |
| 5,178,257 | A | * 1/1993 | Cross | 198/465.1 |
| 5,358,495 | A | * 10/1994 | Lynn | 604/171 |
| 5,443,081 | A | * 8/1995 | Klosterman | 600/585 |
| 5,611,438 | A | 3/1997 | Banerian | |
| 5,634,475 | A | * 6/1997 | Wolvek | 600/585 |
| 5,730,150 | A | * 3/1998 | Peppel et al. | 600/585 |
| 5,738,213 | A | * 4/1998 | Whiting et al. | 206/364 |
| 5,769,222 | A | 6/1998 | Banerian | |
| 5,843,002 | A | * 12/1998 | Pecor et al. | 600/585 |
| 6,047,825 | A | 4/2000 | Samuels | |
| 6,231,564 | B1 | 5/2001 | Gambale | |

* cited by examiner

Primary Examiner—Teresa Walberg
Assistant Examiner—Leonid M. Fastovsky
(74) Attorney, Agent, or Firm—Pierce Atwood

(57) ABSTRACT

A medical guide wire containment device having a housing for receiving and retaining one or more guide wires. The housing includes one or more isolation chambers, each of which is designed to accept therein at least one guide wire. The isolation chambers include fixed guides to cause the wire to coil up therein with minimal entanglement. The isolation chambers also include a receiving funnel and a port centered in the funnel. The port is configured to allow the healthcare provider to pass the guide wire into the isolation chamber and to draw it out of the isolation chamber. An optional wiping sponge is affixed within the chamber behind the receiving port to wipe the guide wire as it enters and exits the isolation chamber. A wetting solution such as heparinized saline is retained within the housing to keep the guide wire clean and wetted. The housing may include a stabilization base to minimize the possibility of the housing tipping over.

17 Claims, 4 Drawing Sheets

MEDICAL GUIDE WIRE CONTAINMENT DEVICE

CROSS-REFERENCE TO RELATED APPLICATION

This application claims the priority benefit of provisional application Ser. No. 60/222,508 filed Aug. 2, 2000, of the same title and by the same inventor.

BACKGROUND OF THE INVENTION

1. Field of the Invention

The present invention relates to containers for holding and dispensing medical guide wires. More particularly, the present invention relates to a modular containment device including a wire containment well and wiring dispensing/insertion port.

2. Description of the Prior Art

Guide wires are used for a wide array of medical procedures, or "interventional" cases. Such wire-guided procedures include, but are not limited to, angiography, cardiac procedures, non-vascular interventional procedures (ERCP), cystoscopic procedures, etc. The guide wires are traditionally supplied in sterile packages in thin plastic spiral housings. Once a package is opened, the housing is flushed with a sterilizing solution to wet the wire. The wire is used to position a medical device, such as a catheter, in a patient. After the wire is used in a particular procedure, it is removed from the catheter or device (and, thus, the patient) and wiped off manually. Next, it is either coiled up and placed into a saline-filled bowl, placed under a towel, or simply left in the medical procedure field, i.e., on the patient, on a surgical tray, etc.

It can readily be seen that for most medical procedures, particularly those common ones where multiple guide wires are required, it is not unusual for guide wires to become lost, contaminated, dropped, or difficult to sort, find, or obtain. In fact, it is common during a busy case that upwards of 5–6 wires may be used. Conventional wire retention bowls, with or without internal rims, are often loaded with all the coiled wires of a procedure. They often become tangled or impossible to differentiate among for specific uses during the procedure. That is, there may be several different types of wires in play, and those wires may differ by tip shape or stiffness, or by thickness differences that may not be apparent to the naked eye. It can be difficult to rapidly untangle or find them when needed. This can lead to delay, danger to the patient, or loss of access. Lost or contaminated wires add to increased costs. For example, one commercially available guide wire, sold under the name GlideWire™ can cost $40 or more for a single wire. Given the thousands of procedures requiring many wires, the cost associated with lost or unusable wires can be significant. Further, they add to procedure clutter, often being laid on top of a medical table and thereby limiting access to other items on the table (catheters, other guide wires, surgical blades, syringes, etc.) As a result, the risk of injury resulting from unintended contact with needles or blades underneath the jumbled wires is greatly increased.

Therefore, what is needed is a device or system for maintaining medical guide wires in an organized manner. Further, what is needed is such an organizing device or system that reduces the time required to clean the wires for re-use during a procedure. Given the number of procedures involving the use of one or more guide wires, the device or system should preferably be relatively inexpensive and easy to use.

SUMMARY OF THE INVENTION

In view of the foregoing, it is an object of the present invention to provide a device or system for maintaining medical guide wires in an organized manner. Further, it is an object of the present invention to provide such an organizing device or system that reduces the time required to clean the wires for re-use during a procedure. It is also an object of the present invention to provide such a device or system that is relatively inexpensive and that is easy to use. These and other objects are achieved with the present invention, which is a guide wire container that provides rapid and secure access to one or more guide wires.

The container may be formed as a single housing or a plurality of housing that may be detachably coupled together. Each housing is capable of holding one or more guide wires. Each housing may have a single wire holding compartment or a plurality of isolated chambers, with each isolation chamber designed to retain one wire or more as desired. Each housing may include engagement means including, but not limited to, hook-and-loop connectors, tongue-in-groove interfaces, clasps, so that multiple housings may be removably linked to one another. The number of housings and the number of isolation chambers, if any, forming the container is dependent upon the total number of individual guide wires desired for a particular procedure. That is, the unit or container may alternatively be designed to fit together in a modular fashion like cassette or CD racks. In that way, if the procedure unexpectedly requires additional wires, modular units may readily be added to the original set.

The container includes one or more top surface sealing elements, such as Luer Lok™ (shown) or catheter tips, for example. For the embodiment of the container where isolation chambers are employed, each such chamber preferably has its own sealing element. The sealing element is a removable closure device designed to seal container fill ports. When opened, a container fill port may be used to fill or prime the container with an appropriate fluid such as heparinized saline.

Individual wires, when removed from their original packaging, are inserted into the container through a wire access port on a front surface of the container. The wire access port includes a port hole sized to enable movement of the wire into and out of the port, a sealing membrane to minimize entry into the container of any fluids, contaminants, etc., that may be located on the wire, and a funnel port to facilitate directing the wire back into the container. The alternative isolation chambers may be guide devices that ensure the wire spirals into a narrowed area to avoid entanglement with adjacent wires.

In order to insert a wire into the container of the present invention, it is pushed back-end first against the membrane. The membrane may be fabricated of latex, silicon, or other suitable material. A wiping sponge positioned behind the membrane in the entryway of the container, is preferably saturated with water or suitable cleaning solution. This automatically wipes blood off the wire, eliminating the requirement to employ a healthcare provider to perform that function. In the process, the wire is pushed all the way in until a small amount, such as about 1–2 cm, remains external to the membrane. This makes the shape of the particular guide wire visible at a glance.

Using the container system of the present invention, individual medical guide wires may be held in place in a suitably coiled arrangement for easy removal and re-use, isolated from other wires, and bathed in heparinized saline.

When a particular wire is needed, it is simply pulled out through the sponge, again wiping off any clot/debris and providing the user with a clean, ready-to-use wire without having to struggle to find it, to remove it from the housing, or to remove it from a bowl. The individual wire access ports may be sized as required to secure wires of the array of dimensions used in medical procedures, including those in the 0.014–0.038 cm diameter range. Sterile stickers with wire gauge, tip shape, and hydrophilicity information indicated may be applied to the container adjacent to the individual wire ports. These identification stickers could be used to speed identification of the wires during the procedure. The container, or one or more of a set of individual containers coupled together, may include a weighted base or other suitable means to ensure that it will remain fixed in a desired position and only moved intentionally.

The present guide wire containment device may be employed on every medical procedure tray. It may be fabricated of inexpensive materials, has no moving parts, and is simple to use. It is modular and disposable. It automatically cleans the wire each time it is used. It fits in far less space than a sterile bowl or random pile of coiled wires, towels, or housings. It can be made in a variety of sizes to accommodate different space restrictions and/or special wire needs, such as some exchange wires and endoscopic/cystoscopic wires that can be even longer than angiographic exchange wires, for example. It is also to be noted that the container of the present invention may be employed, with some modification apparent to those skilled in the art, to house catheters.

These and other advantages of the present invention will be understood upon review of the drawings, the detailed description, and the appended claims.

DETAILED DESCRIPTION OF PREFERRED EMBODIMENTS

A guide wire containment device 10 of the present invention is illustrated in

Figure 1:
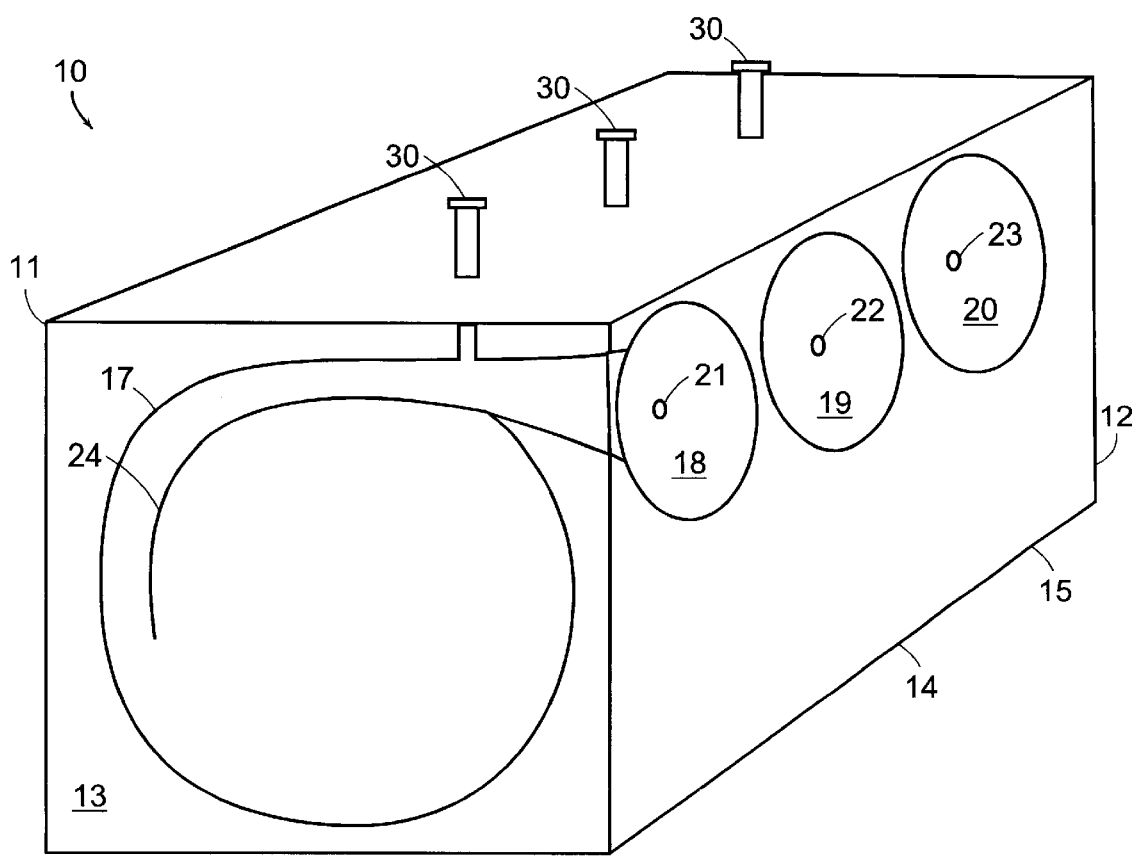
FIG. 1 is a perspective view of a simplified representation of the guide wire containment device of the present invention, showing a single housing with a plurality of isolation chambers.
Figure 2:
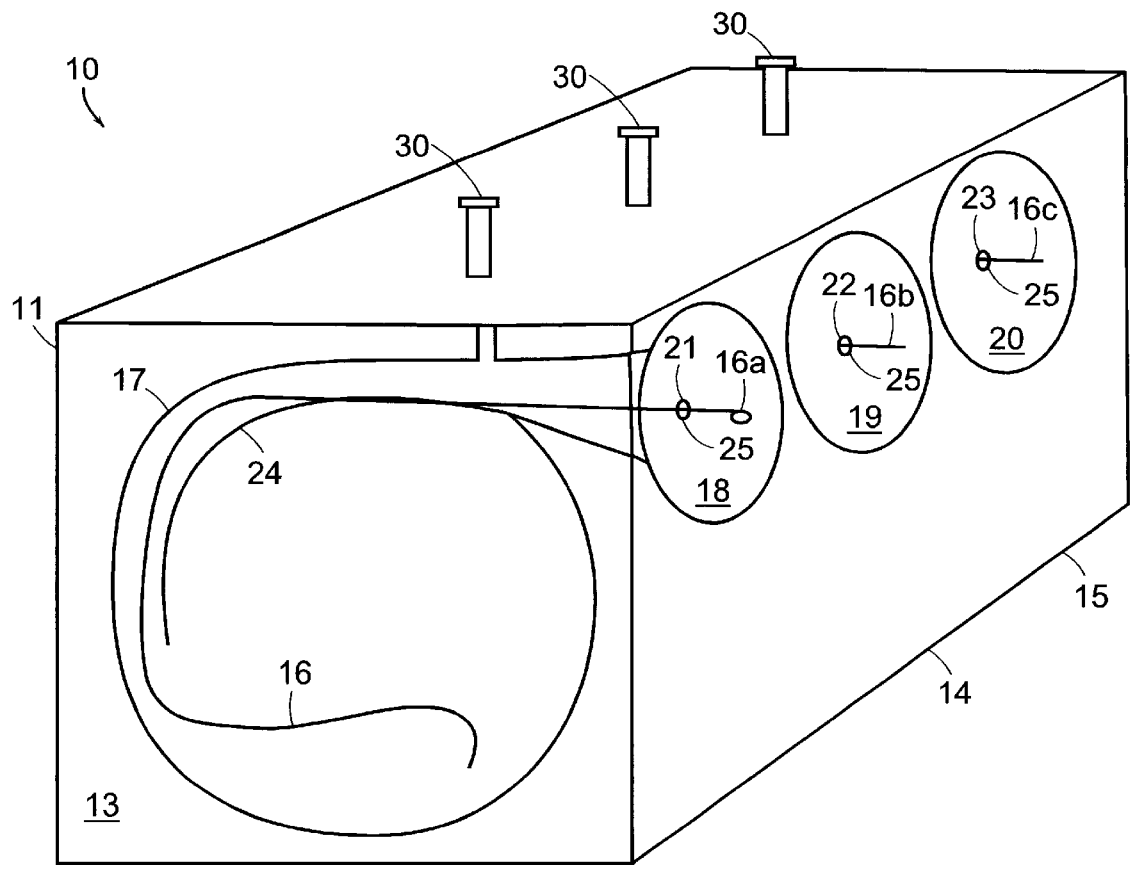
FIG. 2 is a perspective view of a simplified representation of the guide wire containment device shown in FIG. 1 with a guide wire in place in a first isolation chamber.
Figure 3:
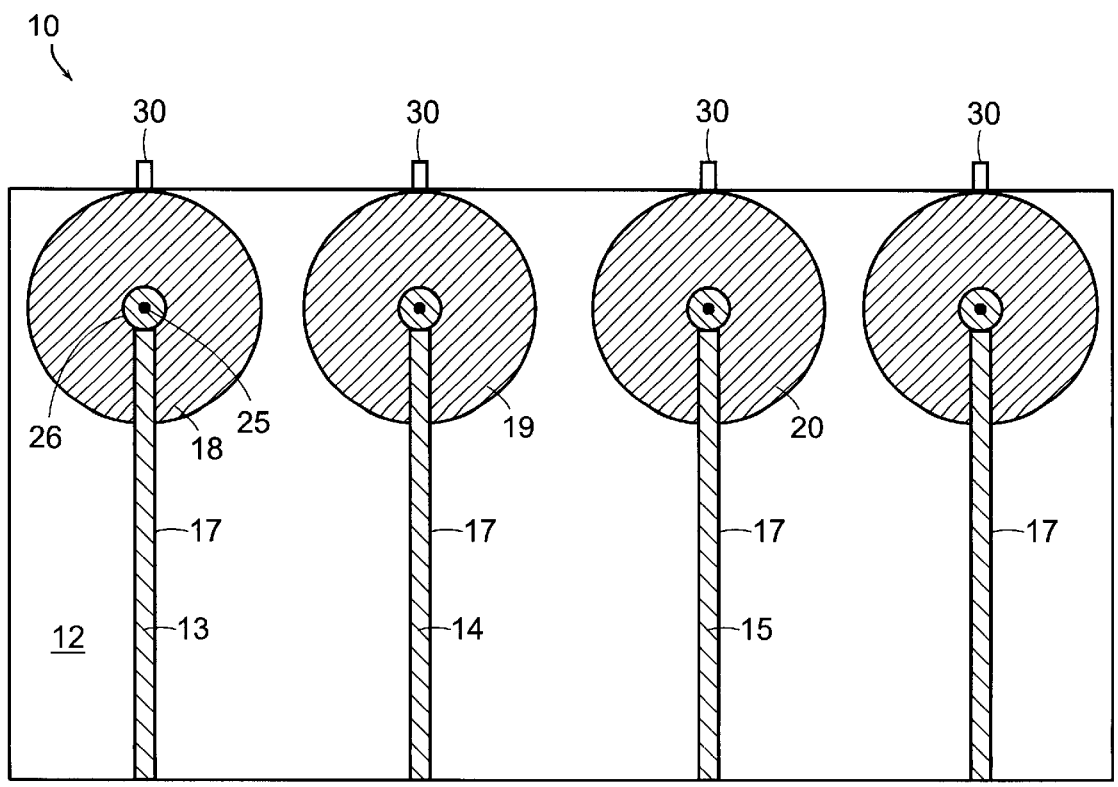
FIG. 3 is a front view of a simplified representation of the containment device of the present invention showing four isolation chambers instead of three.

FIGS. 1–3. The device 10 includes a housing 11 having one or more guide location zones 12 that may be within a common interior region of the housing 11 or it may include a plurality of isolation chambers, such as a first isolation chamber 13, a second isolation chamber 14, and a third isolation chamber 15, as shown. The housing 11 is preferably fabricated of a non-metallic material, but may be fabricated of any material capable of securely retained within a sterilizing solution. The material for the housing 11 must be suitably sterilized when it is to be used in a procedure. The housing 11 may have a weighted base region to ensure that it remains in a desired position and cannot be unintentionally knocked over, at least not easily or not when being manipulated for its intended purpose of passing guide wires into and out of the housing 11 and its interior regions.

While it is contemplated that one or more guide wires such as guide wire 16 shown in FIG. 2 may be retained within the housing 11 in a single common interior region, the device 10 preferably includes the individual isolation chambers such as chambers 13–15. It is to be understood that the housing 11 may be formed with more or fewer isolation chambers than illustrated in the accompanying drawings. The isolation chambers are configured to maintain therein individual guide wires, which guide wires may be of a variety of lengths. For that reason, each isolation chamber is preferably sized of sufficient dimensions to be able to retain therein even the longest of guide wires. The individual chambers 13–15 are preferably cartridge-like structures that may be fabricated of relatively stiff or, alternatively, relatively flexible material, such as a plastic material. They may be rectangular, square, or of cylindrical shape as shown in FIGS. 1–2. Further, the isolation chambers 13–15 must be fabricated of material that cannot be pierced by the guide wire 16. As shown in FIG. 2, tips that are configured the same as the wire, such as tip 16b, may form part of the guide wire, preferably provided that a small portion of the guide wire remains external to the housing 11.

With continuing reference to FIGS. 1–3, the isolation chambers 13–15 may be formed with perforated sidewalls 17 so that a wetting solution, such as heparinized saline, may be inserted into the housing 11 and fills the chambers 13–15 through such perforations. The perforations must be large enough to allow the solution to pass therein but small enough to prevent the guide wire from catching on the rims of the perforations. Alternatively, the sidewalls 17 and most of the body of the chamber are solid such that the chambers 13–15 must be filled with the solution individually. In that configuration, the housing 11 is effectively a means to retain a plurality of independently functional guide wire retaining isolation chambers. Filling ports 30 form part of the housing 11 or individual chambers 13–15, as shown, in order to allow filling of the housing 11 or the isolation chambers 13–15 with the saline solution. A Luer Lok™/catheter tip combination may form the filling ports 30. The isolation chambers 13–15 are preferably modular in some manner so that they may be easily replaced and are preferably used for one procedure in order to maximize safety. They are preferably individually marked with unique identifiers to immediately inform the user of the particular wire retained therein.

In order to facilitate the insertion and removal of a guide wire such as guide wire 16 into an isolation chamber, the housing 11 includes for each isolation chamber a receiving funnel such as funnels 18–20 shown in FIGS. 1–3. The funnel acts as a transition structure to enable a healthcare provider to easily insert the guide wire 16 into an entry port, such as entry ports 21–23, of the isolation chambers 13–15. The ports 21–23 may be of differing size as a function of the particular diameter of the guide wires to pass therethrough. The funnels 18–20 may either be positioned within the housing 11 as shown and substantially form part of the respective individual isolation chambers 13–15, or may alternatively be located exterior to the housing 11 and removably attachable to the individual isolation chambers 13–15. As shown in FIG. 2, the isolation chamber 13, as like the others, includes a preliminary guide 24 that forces the guide wire 16 to curve in a curling manner around the inner perimeter as it enters the chamber 13, as shown in FIG. 3. Use of the fixed guide 24 in the isolation chamber ensures that the guide wire 16 is substantially less likely to become entangled in itself as it is passed into the isolation chamber selected.

Figure 4:
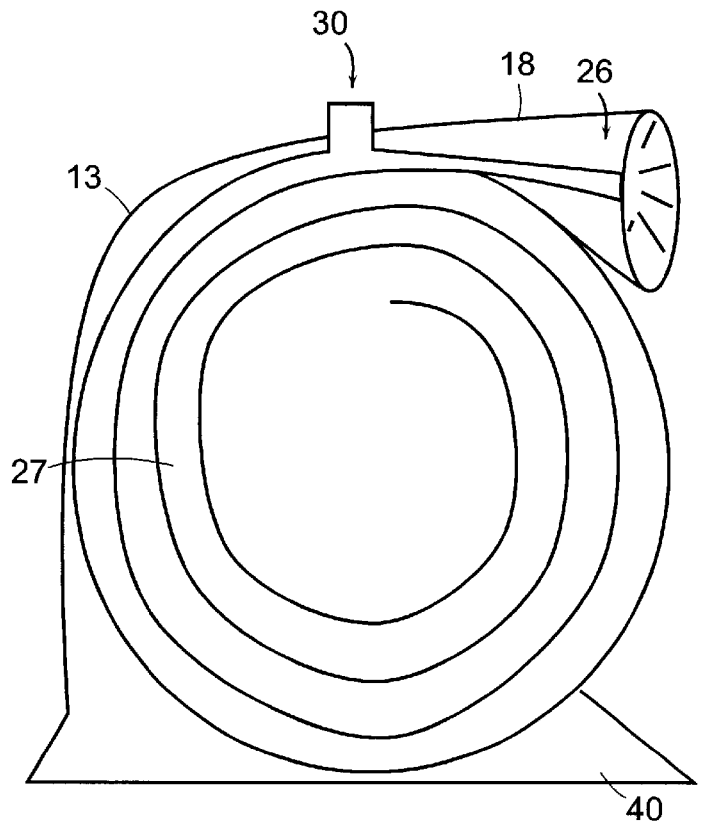
FIG. 4 is a detailed side view of an isolation chamber of the present invention with a guide wire contained therein.
Figure 5:
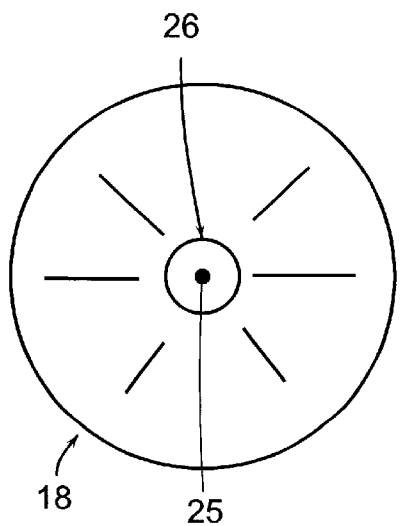
FIG. 5 is a front view of the isolation chamber shown in FIG. 4.

As illustrated in FIGS. 4 and 5, any one or more of the funnels 18–20 preferably includes a tear-resistant membrane 25 to assist in directing the guide wire 16 into the isolation chamber, such as isolation chamber 13. Further, within the isolation chamber 13, an optional wiping sponge 26, is preferably coupled to the membrane 25 at the port. The sponge 26 is coupled to the membrane 25 at the port 21 within the chamber 13 in a manner that causes fluid on the guide wire 16 to be removed as the guide wire 16 enters or exits the chamber 13. Additionally as shown in FIG. 4, rather than a guide such as fixed guide 24 shown in FIG. 3, the isolation chamber 13 may include a fixed spiraling guide 27 that establishes a fixed pathway to ensure the guide wire 16 will spiral in a selected manner without entanglement. That is particularly desirable for very long guide wires.

It is to be noted that the individual isolation chambers 13–15 may have their own weighted bases, such as base 40. The base 40 may either be independent of the region of the chamber having the sterilizing solution and affixed thereto, or it may be integral with that region and may have substantially wider dimensions to provide stability.

The device 10 of the present invention may be used to resolve all of the existing problems associated with dry guide wires, multiple wires becoming entangled, and the difficulty of maneuvering individual guide wires through sterilizing solution and into and out of the procedure. To use the device 10, the healthcare provider may begin with a guide wire by inserting it into a port of an isolation chamber, such as port 21 of isolation chamber 13. The guide wire 16 is retained within the isolation chamber 13 in a substantially uniformly spiraled manner for ease of withdrawal. The isolation chamber 13 preferably includes heparinized saline, as earlier noted. When the guide wire 16 is to be used in a procedure, the tip 16a of the guide wire 16 is pulled to pull the guide wire 16 through the wiping sponge 26 and out through the membrane 25 of the funnel 18. The guide wire 16 may either be completely withdrawn from the chamber 13 or a portion may be left therein. If completely withdrawn, the guide wire 16 may be re-inserted into the chamber 13 via the chamber port 21. Upon return, the wiping sponge 26 removes excess matter from the wire 16 as it passes into the sterilizing solution of the chamber 13, ready for subsequent use during the procedure, if desired. Upon completion of the process, which may involve the use of a plurality of different wires each retained within its own chamber, the entire device 10 may be discarded. Alternatively, if in a modular form, only used portions may be discarded.

While the invention has been described with reference to a particular example embodiment, it is intended to cover all modifications and equivalents as described in the following claims.

What is claimed is:

1. A guide wire retaining device comprising a housing having at least one isolation chamber for storing guide wires therein in a manner that permits extraction with minimal entanglement, wherein said isolation chamber includes means for longitudinally receiving a guide wire.

2. The retaining device as claimed in claim 1 wherein said means for longitudinally receiving the guide wire includes a port in a wall of said housing.

3. The retaining device as claimed in claim 1 wherein said means for longitudinally receiving the guide wire includes a funnel-shaped opening and a port substantially centered in said funnel-shaped opening.

4. The retaining device as claimed in claim 3 wherein said funnel-shaped opening includes a membrane positioned about said port.

5. The retaining device as claimed in claim 1 wherein said isolation chamber includes a wiping sponge therein configured to contact a guide wire passing into and out of said isolation chamber.

6. The retaining device as claimed in claim 1 further comprising a fixed guide within said isolation chamber.

7. The retaining device as claimed in claim 1 further comprising a spiral guide within said isolation chamber.

8. The retaining device as claimed in claim 1 wherein said housing is designed to retain a sterile wetting solution.

9. The retaining device as claimed in claim 8 wherein said sterile wetting solution is heparinized saline solution.

10. The retaining device as claimed in claim 1 wherein said isolation chamber includes a fill port for receiving sterile solutions.

11. The retaining device as claimed in claim 10 wherein each fill port includes a catheter tip.

12. The retaining device as claimed in claim 1 wherein said housing is fabricated of a non-metallic material.

13. The retaining device as claimed in claim 1 further comprising a stabilizing base.

14. The retaining device as claimed in claim 13 wherein said stabilizing base forms an integral part of said housing.

15. The retaining device as claimed in claim 13 wherein said stabilizing base is detachably connectable to said housing.

16. The retaining device as claimed in claim 1 further comprising a second isolation chamber for storing guide wires therein in a manner that permits extraction with minimal entanglement, wherein said second isolation chamber includes a second means for longitudinally receiving a guide wire.

17. The retaining device as claimed in claim 16 further comprising a sidewall separating said isolation chambers.

* * * * *